(12) United States Patent
Everling (10) Patent No.: US 11,179,199 B2
(45) Date of Patent: Nov. 23, 2021

(54) ALIGNING A CARDIAC MODEL (71) Applicant: St. Jude Medical, Cardiology Division, Inc., St. Paul, MN (US)

(72) Inventor: Bruce R. Everling, Eagan, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 560 days.

(21) Appl. No.: 15/578,379

(22) PCT Filed: May 23, 2016

(86) PCT No.: PCT/US2016/033696
§ 371 (c)(1),
(2) Date: Nov. 30, 2017

(87) PCT Pub. No.: WO2016/196047
PCT Pub. Date: Dec. 8, 2016

(65) Prior Publication Data
US 2018/0132938 A1 May 17, 2018

Related U.S. Application Data

(60) Provisional application No. 62/170,513, filed on Jun. 3, 2015.

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0044* (2013.01); *A61B 5/061* (2013.01); *A61B 5/062* (2013.01);
(Continued)

(58) Field of Classification Search
None
See application file for complete search history.

(56) References Cited

U.S. PATENT DOCUMENTS 7,263,397 B2    8/2007  Hauck et al.
7,697,972 B2 *  4/2010  Verard ............... A61B 1/00071
                                                  600/407
(Continued)

FOREIGN PATENT DOCUMENTS

EP    2732765 A1   5/2014
WO    2013112366 A1   8/2013

*Primary Examiner* — Oommen Jacob
*Assistant Examiner* — Shahdeep Mohammed
(74) *Attorney, Agent, or Firm* — Dykema Gossett PLLC (57) ABSTRACT

A method (94) for aligning a cardiac model can include receiving (95) an initial position signal from three position sensors (17, 39, 40) disposed along a distal end of a coronary sinus catheter (13) positioned in a coronary sinus (41) of a heart (10). The method (94) can include receiving (96) a subsequent position signal from the three position sensors (17, 39, 40). The method (94) can include determining (97) a positional change vector based on a change in position between an initial position associated with the initial position signal and a subsequent position associated with the subsequent position signal. The method (94) can include shifting (98) a point of interest associated with a cardiac model, using the positional change vector. The method (94) can include dynamically aligning (100) the cardiac model based on an updated position of the three position sensors (17, 39, 40).

11 Claims, 8 Drawing Sheets

(51) Int. Cl.
*A61B 5/06* (2006.01)
*G16H 50/50* (2018.01)
*G16H 30/40* (2018.01)
*A61B 5/283* (2021.01)
*A61B 5/318* (2021.01)
*A61B 5/339* (2021.01)
*A61B 5/107* (2006.01)

(52) U.S. Cl.
CPC .............. *A61B 5/065* (2013.01); *A61B 5/068* (2013.01); *A61B 5/339* (2021.01); *A61B 5/6852* (2013.01); *G16H 30/40* (2018.01); *G16H 50/50* (2018.01); *A61B 5/107* (2013.01); *A61B 5/283* (2021.01); *A61B 5/318* (2021.01); *A61B 2034/105* (2016.02)

(56) References Cited

U.S. PATENT DOCUMENTS

| | | | |
|---|---|---|---|
| 2004/0097806 A1* | 5/2004 | Hunter | A61B 1/00071 600/434 |
| 2009/0253985 A1* | 10/2009 | Shachar | A61B 1/018 600/424 |
| 2012/0065481 A1* | 3/2012 | Hunter | A61B 1/00071 600/301 |
| 2012/0197111 A1 | 8/2012 | Bar-Tal et al. | |

* cited by examiner

ALIGNING A CARDIAC MODEL

CROSS-REFERENCE TO RELATED APPLICATION

This application claims the benefit of and priority to U.S. provisional patent application No. 62/170,513, filed 3 Jun. 2015, which is hereby incorporated by reference as though fully set forth herein.

BACKGROUND a. Field of the Invention

The present disclosure relates generally to aligning a model with a position of an organ.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. A medical device can be threaded through a vasculature of a patient to a site where the diagnostic, therapeutic, mapping, and/or ablative procedure to diagnose and/or correct the condition is performed.

Sensors (e.g., electrodes, magnetic positioning sensors) can be placed on the medical device, which can receive signals that are generated proximate to the patient from a device. Based on the received signals, an orientation and/or position of the medical device within a heart can be computed. Further, a model of the heart can be constructed from position data gathered from the sensors.

BRIEF SUMMARY

Various embodiments herein provide a method for aligning a cardiac model. In at least one embodiment, the method can include receiving an initial position signal from three position sensors disposed along a distal end of a coronary sinus catheter positioned in a coronary sinus of a heart. The method can include receiving a subsequent position signal from the three position sensors. The method can include determining a positional change vector based on a change in position between an initial position associated with the initial position signal and a subsequent position associated with the subsequent position signal. The method can include shifting a point of interest associated with a cardiac model, using the positional change vector. The method can include dynamically aligning the cardiac model based on an updated position of the three position sensors.

In various embodiments, instructions for aligning a cardiac model are executable by a computer to receive an initial position signal from a proximal position sensor, a distal position sensor, and a medial position sensor. The proximal position sensor can be disposed in a coronary sinus of a heart. The medial position sensor can be disposed orthogonally to a computed line extending between the proximal position sensor and the distal position sensor. A subsequent position signal can be received from the proximal position sensor, the distal position sensor, and the medial position sensor. A change in position of the proximal position sensor can be determined based on the initial position signal and the subsequent position signal. A change in a position of the medial position sensor with respect to the line extending between the proximal position sensor and the distal position sensor can be determined. A cardiac model can be shifted based on the change in position of the proximal position sensor and the change in the position of the medial position sensor with respect to the line extending between the proximal position sensor and the distal position sensor.

Various embodiments herein provide a system for aligning a cardiac model. The system includes an elongate catheter that includes a proximal end and a distal end, wherein a proximal position sensor, a distal position sensor, and a medial position sensor are disposed on the distal end of the catheter, the distal end being configured to deflect. An initial position signal can be received from the proximal position sensor, the distal position sensor, and the medial position sensor. A subsequent position signal can be received from the proximal position sensor, the distal position sensor, and the medial position sensor. A change in a position of the proximal position sensor can be determined based on the initial position signal and the subsequent position signal. A change in a position of the distal position sensor can be determined with respect to the proximal position sensor based on the initial position signal and the subsequent position signal. A change in a position of the medial position sensor can be determined with respect to a line between the proximal position sensor and the distal position sensor, based on the initial position signal and the subsequent position signal. A cardiac model can be shifted based on the change in position of the proximal position sensor, the distal position sensor, and the medial position sensor.

DETAILED DESCRIPTION

Figure 1:
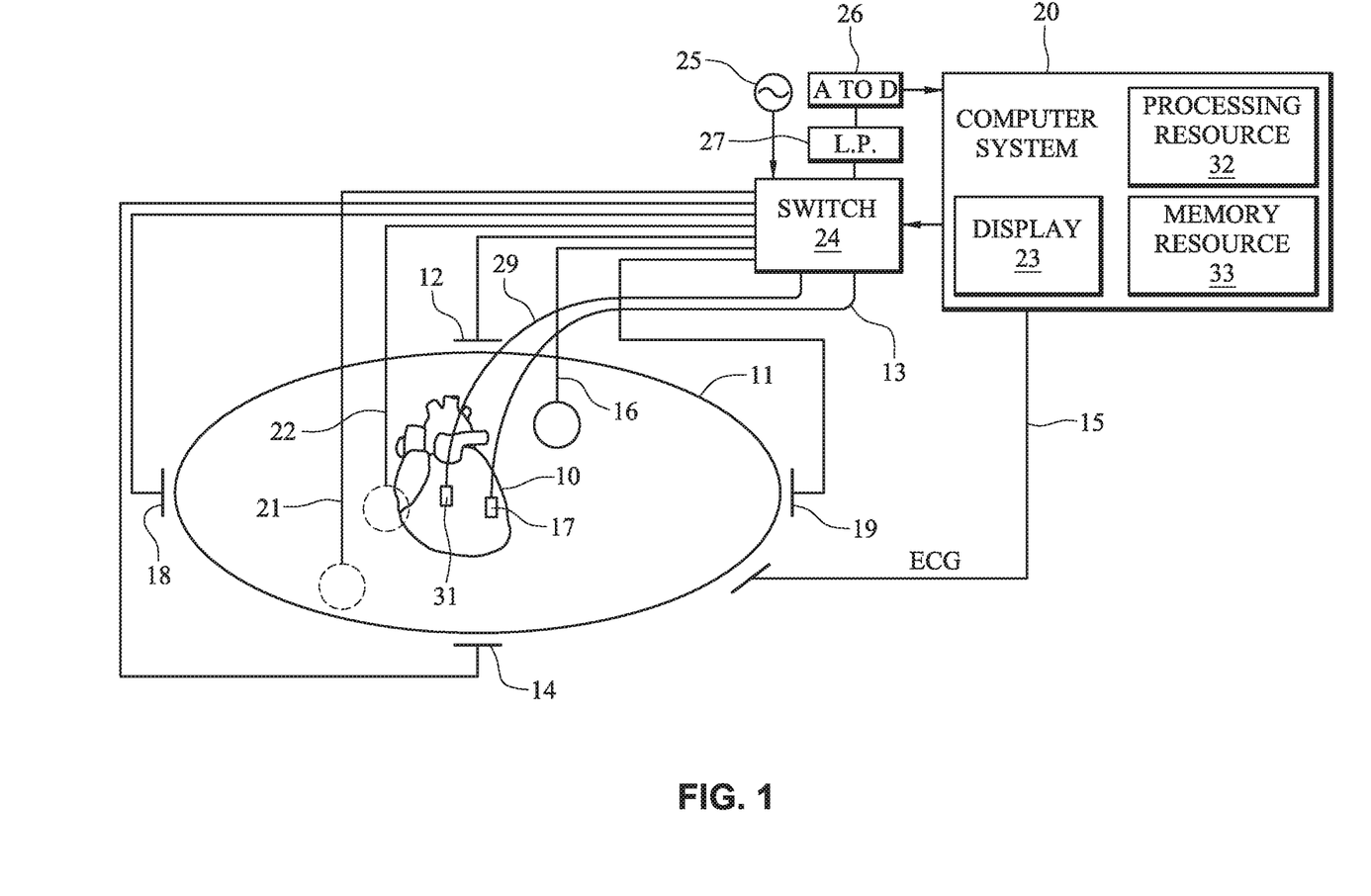
FIG. 1 is a diagrammatic view of an exemplary system for performing one or more diagnostic or therapeutic procedures, wherein the system comprises an impedance based medical positioning system, in accordance with embodiments of the present disclosure.

Referring now to the drawings wherein like reference numerals are used to identify identical components in the various views, FIG. 1 is a diagrammatic overview of a catheter system in which the invention may be practiced. The system may comprise various visualization, mapping and navigation components as known in the art, including among others, for example, an EnSite™ Velocity™ Cardiac Mapping and Visualization System commercially available from St. Jude Medical, Inc., or as seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. The system may be used in connection with or for various medical procedures, for example, mapping of the heart and/or cardiac ablation procedures. Although reference is made to cardiac mapping of the heart, one or more aspects of the present disclosure may apply to other anatomic structures.

The catheter system includes a diagrammatic depiction of a heart 10 of a patient 11. The system includes the ability to receive a plurality of catheter locations as the catheter distal end is swept around and within a chamber of the heart. For this purpose, FIG. 1 shows an exemplary catheter localization system of the type based on externally-applied orthogonal electric fields which are used to determine the location of one or more catheter position sensors. Such a system is known generally in the art (e.g., an EnSite NAVX™ Navigation and Visualization System). It should be understood, however, that this embodiment is exemplary only and not limiting in nature. Other technologies for determining the location in 3D space of a catheter, such as the MediGuide™ system, may be used in practicing the present invention, including for example, the CARTO navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more position sensors. The position sensors can include one or more electrodes configured to detect ono or more characteristics of an electrical field, for example in the case of an impedance-based localization system, or alternatively, one or more coils (e.g., wire windings) configured to detect one or more characteristics of a magnetic field, for example, in the case of a magnetic-field based localization system.

It should be further understood that in some localization systems, one or more position sensors may collectively define the sensor. The one or more position sensors may be provided on a distal end of a catheter and the localization system may be configured to obtain location information from the one or more position sensors. The localization system may compute a distal location of the catheter using not only the received location information, but also a geometrical relationship between the one or more position sensors providing the location information and the distal location on the catheter (e.g., one piece of geometrical information may be the ring electrode to tip distance). Finally, the localization system may use the computed location, as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1, in the illustrated impedance-based localization system embodiment, three sets of surface electrodes (e.g., applied via a patch) are shown: X-axis electrodes 12, 14; Y-axis electrodes 18, 19; and Z-axis electrodes 16, 22. Additionally, an additional surface electrode 21 (e.g., applied via a "belly" patch) may be used. The surface electrodes are all connected to a switch 24. A representative catheter 13 is shown, which has a single distal electrode 17, which may be referred to herein as a "roving" or "measurement" electrode. In some embodiments, the catheter 13 can be a coronary sinus catheter or a right ventricle apex catheter. The electrode 17 may define the position sensor in this embodiment, but as alluded to above, many variations are possible and the catheter 13 can include multiple position sensors, as discussed further herein. FIG. 1 also shows a second, independent catheter 29 with a fixed reference electrode 31, Which may be stationary on the heart 10 for calibration purposes.

FIG. 1 further shows a computer system 20, a signal generator 25, an analog-to-digital converter 26 and a low-pass filter 27. The computer system 20 can utilize software, hardware, firmware, and/or logic to perform a number of functions described herein. The computing system 20 can be a combination of hardware and instructions to share information. The hardware, for example can include processing resource 32 and/or a memory resource 33 (e.g., non-transitory computer-readable medium (CRM) database, etc.). A processing resource 32, as used herein, can include a number of processors capable of executing instructions stored by the memory resource 33. Processing resource 32 can be integrated in a single device or distributed across multiple devices. The instructions (e.g., computer-readable instructions (CRI)) can include instructions stored on the memory resource 33 and executable by the processing resource 32 for aligning a cardiac model. The computer system 20 is discussed further in relation to FIG. 8.

The computer system 20 is configured to control the signal generator 25 in accordance with predetermined strategies to selectively energize various pairs of surface electrodes. In operation, the computer system 20 is configured to obtain raw patch data (i.e., voltage readings) via the filter 27 and A-D converter 26 and use this raw patch data to determine the raw electrode location coordinates in three-dimensional space (X, Y, Z) of a catheter electrode positioned inside the heart 10 or chamber thereof (e.g., such as the roving electrode 17 mentioned above). In some embodiments, a phase of the patient's 11 cardiac cycle can be measured. or otherwise determined when such electrode location coordinates are being received. For this purpose, in an embodiment, most or all of the conventional twelve (12) ECG leads, coupled to body surface electrodes and designated collectively by reference numeral 15, are provided to support the acquisition of an electrocardiogam (ECG) of the patient 11.

Alternatively, a reference electrode positioned in a fixed location in the heart 10, such as fixed reference electrode 31, may be used to provide a relatively stable signal that can be analyzed to determine the cardiac phase of the heart 10 in the cardiac cycle (e.g., placed at the coronary sinus). More generally, another catheter having an electrode, other than the moving or roving catheter, may be placed and maintained in a constant position relative to the heart 10 to obtain a relatively stable signal indicative of cardiac phase. As shown, the ECG leads 15 are coupled directly to the computer system 20 for acquisition and subsequent processing to obtain the phase of the heart 10 in the cardiac cycle. The ECG leads 15 may also be provided to other systems (not shown).

Figure 2:
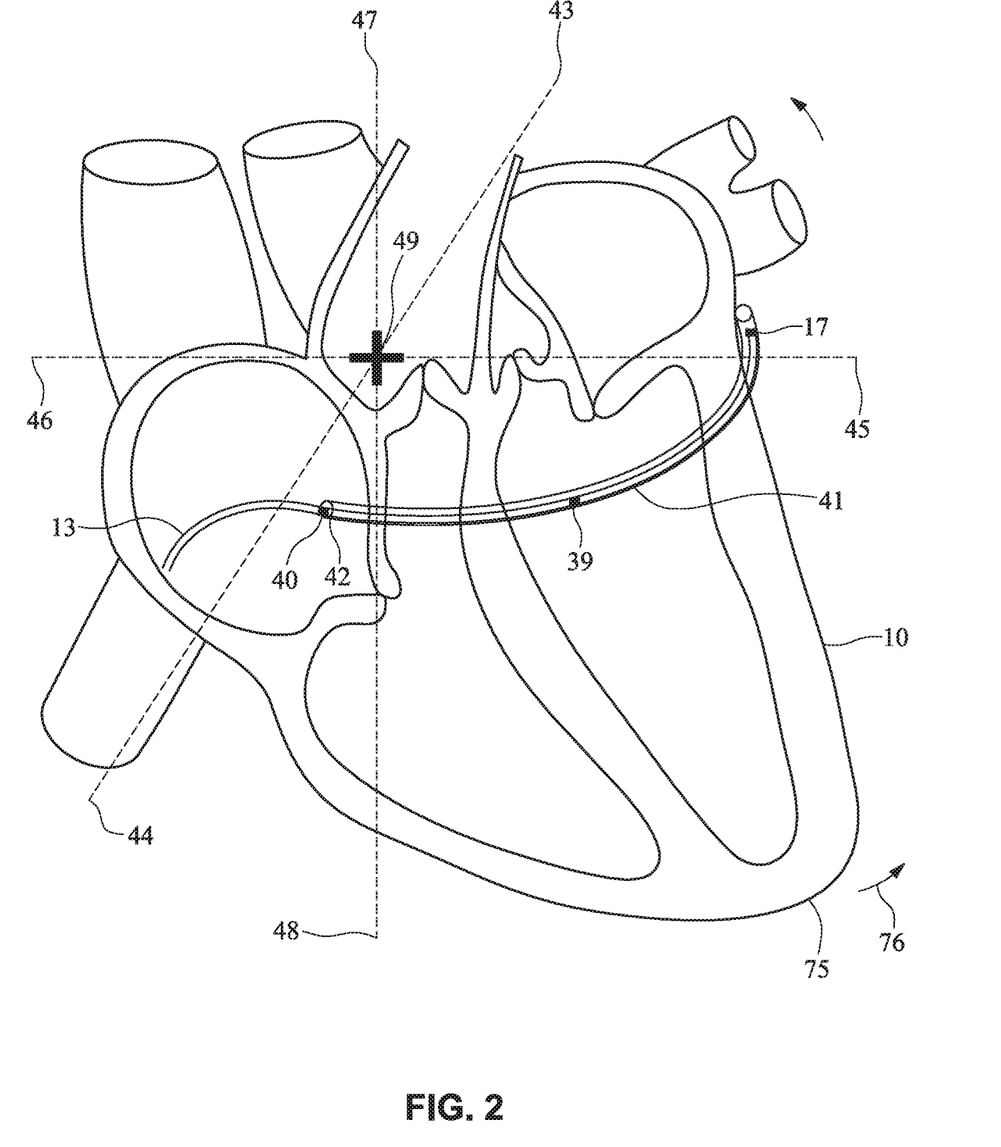
FIG. 2 depicts a heart with a catheter inserted in the coronary sinus of the heart, in accordance with embodiments of the present disclosure.

FIG. 2 shows in greater detail an embodiment of the exemplary catheter 13 of FIG. 1. The catheter 13 may be disposed in the coronary sinus 41 of the heart 10. The invention is not limited to any one type of catheter or catheter-based system or procedure. In addition, as described above, the position sensor, in the described impedance-based localization embodiment, may comprise one or more of the catheter tip electrode and ring electrodes. All location information may be used to improve the determination of a location data point for use in aligning a model with a position of an organ. In some embodiments, all location information may be used to improve the determination of the location data point for use in aligning a cardiac model with a position of the heart.

Some visualization systems can construct a 3-dimensional model of the heart 10 or other anatomic structure. Some visualization systems can capture an additional time dimension and produce 4-dimensional image data and can replay the image data in sequence in order to provide cinematographic loops. These moving images can provide an ability to visualize the beating heart 10 and can, for example, be used by a physician when accessing the heart 10.

However, current procedures that provide a model of the heart 10 can be susceptible to model drift, which can lead to an inaccurate representation of a position of the heart 10 via the model. In an example, the heart 10 can be fixed at a top of the heart via major vessels. These vessels can include the brachiocephalic artery, superior vena cava, right pulmonary arteries, right pulmonary veins, left pulmonary arteries, left pulmonary veins, the brachiocephalic artery, left common carotid artery, and left subclavian artery. Because the heart is fixed at the top, the heart 10 can rotate around a position (e.g., center of rotation 49) generally located in the pulmonary artery to the right of the pulmonic valve, as further shown in FIG. 2.

As further discussed herein, directions with respect to the heart 10 will be discussed in terms of movement about a center of rotation 49. For example, the heart 10 can move with respect to an anterior/posterior axis, for example, the heart 10 can move toward a posterior side 43 or anterior side 44 of the anterior/posterior axis. The heart 10 can move with respect to a left/right axis, for example, the heart 10 can move toward a left side 45 or right side 46 of the left/right axis. The heart 10 can move with respect to a top/base axis, for example, the heart 10 can move toward a top side 47 or base side 48 of the top/base axis. In some embodiments, an apex of the heart 75 can move such that the apex of the heart 75 rotates about the center of rotation 49 toward the posterior side 43, anterior side 44, left side 45, right side 46, top side 47, and/or base side 48.

Visualization systems can be susceptible to catheter drift, which can be caused by a physical movement of the heart 10 with respect to reference positional sensors (e.g., surface electrodes). It has been reported that catheter drift can be more severe in the left atrium versus the right atrium. The catheter drift can be due to a physical movement of the heart 10 versus the reference positional sensor locations as a procedure progresses. In embodiments, movement of the heart 10 can be caused by filling of a patient's bladder during a procedure. For example, if irrigated catheters are used or the procedure is expected to last for more than an hour, the bladder can begin to fill, which can displace other internal organ structures. Because the internal organ structures cannot easily expand, they push up into the lung area, which can move the heart. As the heart moves, it does not move unidirectionally, but can tend to rotate counterclockwise, as viewed from an anterior side 44. This would imply more movement of the left ventricle and atrium. The rotation can be due to the fact that the major vessels can act to hold the upper right side of the heart stationary, which can allow the apex of the heart 75 to rotate towards a top side 47 and counterclockwise, as viewed from the anterior side 44 (in a direction of arrow 76).

In addition, the apex of the heart 75 can rotate as a result of feces and gas buildup in the transverse colon. Feces and gas buildup in the transverse colon can cause excessive movement of the colon, which can directly impact the position of the heart 10. Apnea can also be problematic in regards to movement of the heart. Patients that have apnea can involuntarily stop breathing while a procedure is being performed. This can cause even an unconscious body to automatically react in order to save itself, which can in turn cause unexpected body movement that affects a position of the heart. Further, while a procedure is being performed on a patient, if a physician leans on the patient, or presses on the abdomen of the patient, the internal organs of the patient can be moved, thus affecting a position of the heart. Embodiments of the present disclosure can align a cardiac model of the heart 10 with a position and orientation of the heart 10, thus accounting for the catheter drift. In addition, embodiments of the present disclosure can align a cardiac model of the heart 10 with a position and orientation of the heart 10 to account for movement of the heart due to respiration and cardiac motion.

In some embodiments, as discussed herein, a catheter 13 can be inserted into the coronary sinus 41 of a patient's heart 10. As discussed herein, the catheter 13 can be a coronary sinus catheter. The catheter 13 can be an elongate catheter that includes a proximal end and a distal end and a distal end of the catheter 13 can be configured to deflect. In some embodiments, the catheter 13 can include a plurality of position sensors (e.g., 8 to 10 position sensors). The position sensors can be disposed on the distal end of the catheter 13 and a proximal position sensor, medial position sensor, and distal position sensor can be selected from the plurality of position sensors disposed on the distal end of the coronary sinus catheter 13. The coronary sinus catheter 13 can include a proximal position sensor 40, a medial position sensor 39, and a distal position sensor 17 disposed along a distal end of the coronary sinus catheter 13.

In some embodiments, the distal end of the coronary sinus catheter 13 can be placed in the coronary sinus 41 such that some or all of the position sensors are disposed within the coronary sinus 41. One of the position sensors (e.g., proximal position sensor) located in the coronary sinus ostium 41 of the heart 10 can be selected such that a location signal can be received from the position sensor disposed in the coronary sinus ostium 42. A distal position sensor 17 disposed on the catheter 13 and located towards the left side 45 of the coronary sinus 41 can be selected, such that a location signal can be received from the position sensor disposed in the left side 45 of the coronary sinus 41. In some embodiments, the medial position sensor 39 can be disposed between the proximal position sensor 40 and the distal position sensor 17 and can be selected based on the proximal position sensor 40 and the distal position sensor 17, as further discussed herein.

The coronary sinus 41 can have a slight curve associated with it, such that the medial position sensor 39 is disposed orthogonally to a computed line between the proximal position sensor 40 and the distal position sensor 17 disposed on the coronary sinus catheter 13. The proximal position sensor 40, the medial position sensor 39, and the distal position sensor 17 can provide three points, which can be used for a determination of position and orientation of the heart 10. For example, the proximal position sensor 40 and the distal position sensor 17 can both be disposed on a computed line, which passes through both the proximal position sensor 40 and the distal position sensor 17. The medial position sensor 39 can be disposed off of the computed line that passes through the proximal position sensor 40 and the distal position sensor 17. For example, the medial position sensor 39 can be disposed orthogonally to the computed line that the proximal position sensor 40 and the distal position sensor 17 are disposed on. As such, a rotation of the heart 10 about the computed line that the proximal position sensor 40 and the distal position sensor 17 are disposed on can be determined.

In some embodiments, the memory resource 33 can store computer-readable instructions that, when executed by the processor resource 32 cause the processor resource 32 to receive an initial position signal from the proximal position sensor 40, the distal position sensor 17, and the medial position sensor 39. In some embodiments, the initial position signal can be received from the proximal position sensor 40, the distal position sensor 17, and the medial position sensor 39. In some embodiments, a medial locating signal can be received from the proximal position sensor 40 and the distal position sensor 17. In an example, the medial locating signal can be received before the initial position signal is received from the proximal position sensor 40, the distal position sensor 17, and the medial position sensor 39. The medial locating signal can include a position signal received from the proximal position sensor 40 and the distal position sensor 17. Based on the position signal received from the proximal position sensor 40 and the distal position sensor 17, the medial position sensor 39 can be selected. For example, a computed line between the proximal position sensor 40 and the distal position sensor 17 can be determined. A midpoint of the computed line between the proximal position sensor 40 and the distal position sensor 17 can be determined and the medial position sensor 39 can be selected based off of the midpoint of the computed line, as further discussed herein.

In some embodiments, instructions can be executed by the processor resource 32 to receive a subsequent position signal from the proximal position sensor 40, the distal position sensor 17, and the medial position sensor 39. In some embodiments, a change in a position of the proximal position sensor 40 can be determined based on the initial position signal and the subsequent position signal. For example, as a result of movement of the heart 10, the proximal position sensor 40 located in the coronary sinus ostium 42 can be moved along with the heart 10. In an example, the proximal position sensor 40 can be moved by a physician to maintain the position of the proximal position sensor 40 in the coronary sinus 41 of the heart 10, when the heart 10 moves. In some embodiments, a change in coordinates of the proximal position sensor 40 can be calculated based on the initial position signal and the subsequent position signal received from the proximal position sensor 40. In an example, the change in coordinates of the proximal position sensor 40 can be used to linearly shift a cardiac model so it reflects movement of the heart 10, as discussed further in relation to FIG. 5.

However, if the heart 10 is rotated around the point where the proximal position sensor 40 is located, the difference between the initial position signal and the subsequent position signal may not provide an indication that the heart 10 has moved. Thus, the change in the position of the proximal position sensor 40 may not be determined from the initial position signal and the subsequent position sisal associated with the proximal position sensor 40.

Figure 3:
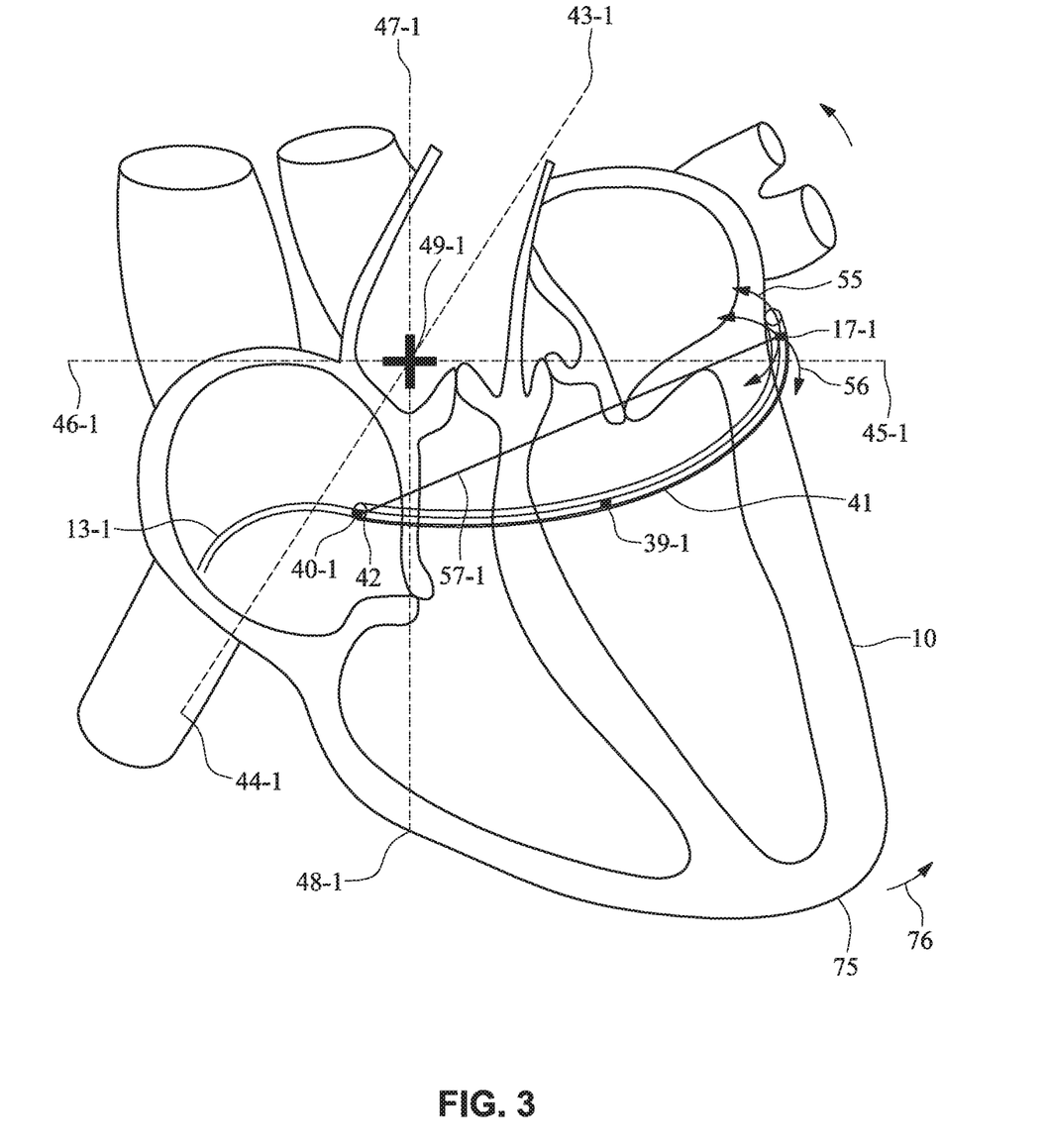
FIG. 3 depicts the heart in FIG. 2 with the catheter inserted in the coronary sinus of the heart and movement of a distal electrode disposed on a distal end of the catheter, in accordance with embodiments of the present disclosure.

FIG. 3 depicts the heart 10 in FIG. 2 with a catheter 13-1 inserted in the coronary sinus 41 of the heart 10 and movement of a distal position sensor 17-1 disposed on a distal end of the catheter 13-1 with respect to a proximal position sensor 40-1 disposed on the distal end of the catheter 13-1, in accordance with embodiments of the present disclosure. In some embodiments, where the heart 10 is rotated around the point where the proximal position sensor 40-1 is located, as discussed herein, the difference between the initial position signal and the subsequent position signal may not provide an indication that the heart 10 has moved. Accordingly, in some embodiments, a change in a position of the distal position sensor 17-1 with respect to the proximal position sensor 40-1 can be determined based on the initial position signal and the subsequent position signal.

In some embodiments, the proximal position sensor 40-1 can serve as a reference position sensor with respect to the distal position sensor 17-1. For example, the proximal position sensor 40-1 can remain in the coronary sinus ostium 42 and the distal position sensor 17-1 can move with respect to the proximal position sensor 40-1. As such, in some examples where the heart 10 is rotated around the point where the proximal position senor 40-1 is located, the distal position sensor 17-1 can still be moved with respect to the proximal position sensor 40-1, thus allowing for a determination of movement of the heart based on the initial position signal and the subsequent position signal received from the proximal position sensor 40-1 and the distal position sensor 17-1.

In some embodiments, a line 57-1 can be computed between the proximal position sensor 40-1 and the distal position sensor 17-1. In some embodiments, a slope of the line 57-1 between the proximal position sensor 40-1 and the distal position sensor 17-1 can be determined, which can be used to determine a change in position of the distal position sensor 17-1 with respect to the proximal position sensor 40-1. For example, if an apex 75 of the heart 10 rotates towards the top side 47-1 or base side 48-1 of the top/base axis in a direction of arrow 55, the slope of the line 57-1 will change. In addition, if the heart 10 rotates towards the posterior side 43-1 or anterior side 44-1 of the anterior/posterior axis, the slope of the line 57-1 will change. Accordingly, a change in the position of the distal sensor 17-1 with respect to the proximal sensor 40-1 can be determined based on the initial position signal and the subsequent position signal.

In some embodiments, a distal position sensor positional change vector can be calculated based on the change in position of the distal position sensor 17-1 with respect to the proximal position sensor 40-1. In an example, the distal position sensor positional change vector can be representative of the change in position of the distal position sensor 39-1 and can be used to rotationally shift a cardiac model so it reflects movement of the heart 10, as discussed further in relation to FIG. 5.

Figure 4:
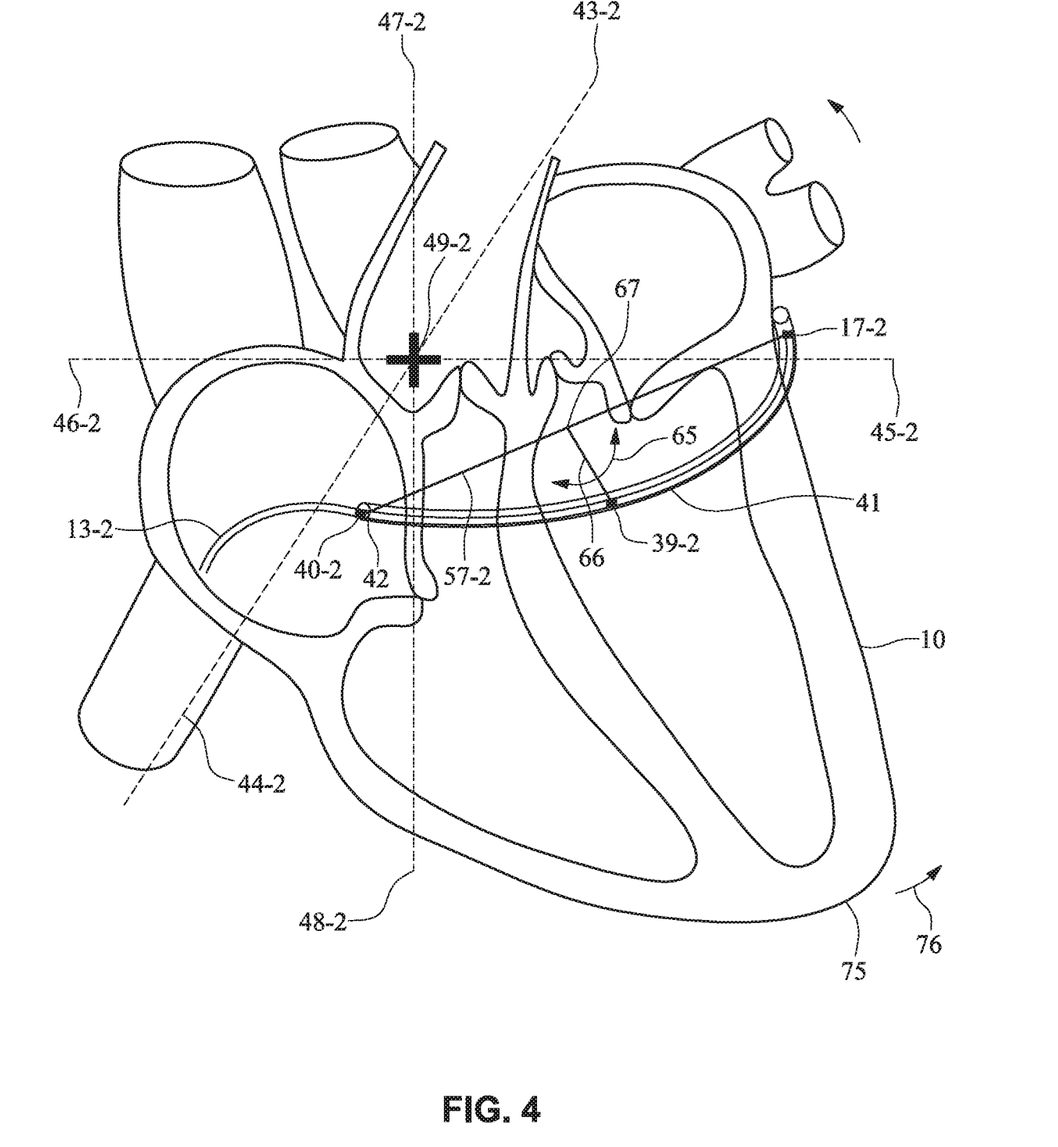
FIG. 4 depicts the heart in FIG. 2 with the catheter inserted in the coronary sinus of the heart and movement of a medial electrode, in accordance with embodiments of the present disclosure.

FIG. 4 depicts the heart 10 in FIG. 2 with a catheter 13-2 inserted in the coronary sinus 41 of the heart 10 and movement of a medial position sensor 39-2 with respect to a medial line 66 between the proximal position sensor 40-2 disposed on the distal end of the catheter 13-2 and the distal position sensor 17-2 disposed on the distal end of the catheter 13-2, in accordance with embodiments of the present disclosure. As discussed herein, in some embodiments, a medial locating signal can be received from the proximal position sensor 40-2 and the distal position sensor 17-2. The medial locating signal can include a position signal received from the proximal position sensor 40-2 and the distal position sensor 17-2. Based on the position signal received from the proximal position sensor 40-2 and the distal position sensor 17-2, the medial position sensor 39-2 can be selected. For example, a line 57-2 (e.g., computed line) between the proximal position sensor 40-2 and the distal position sensor 17-2 can be determined.

A midpoint of the line 57-2 between the proximal position sensor 40-2 and the distal position sensor 17-2 can be determined, and the medial position sensor 39-2 can be selected based off of the midpoint 67 of the line 57-1 In an example, a position of the proximal position sensor 40-2 (e.g., $x_p$, $y_p$, $z_p$) and a position of the distal position sensor 17-2 (e.g., $x_d$, $y_d$, $z_d$) can be determined and the midpoint 67 can be calculated. Based on the midpoint 67, the medial position sensor 39-2 can be selected from a plurality of position sensors disposed on the catheter 13-2. For example, the medial position sensor 39-2 that is selected can be orthogonal to the midpoint 67 or close to orthogonal to the midpoint 67 with respect to the line 57-2. In some embodiments, the medial position sensor 39-2 can be orthogonal to the line 57-2 at a position between the proximal position sensor 40-2 and the distal position sensor 17-2. For example, the medial position sensor 39-2 can be orthogonal to the line 57-2 at a position nearer to the proximal position sensor 40-2 than the distal position sensor 17-2 or nearer to the distal position sensor 17-2 than the proximal position sensor 40-2.

In some embodiments, when the heart 10 rotates about the line 57-2 computed between the proximal position sensor 40-2 and the distal position sensor 17-2, a position of the proximal position sensor 40-2 and the distal position sensor 17-2 does not change, nor does a slope associated with the line 57-2. Thus, even though the heart 10 is rotating about the line 57-2 that the proximal position sensor 40-2 and the distal position sensor 17-2 are collinear with, movement of the heart 10 may not be detected. In some embodiments, the proximal position sensor 40-2 can serve as a reference position sensor with respect to the medial position sensor 39-2. In some embodiments, a change in a position of the medial position sensor 39-2 with respect to the line 57-2 that the proximal position sensor 40-2 and the distal position sensor 17-2 are collinear with can be determined based on the initial position signal and the subsequent position signal.

In an example, if the heart rotates about the line 57-2, the position of the medial position sensor 39-2 will change, which can be used to determine the change in position of the medial position sensor 39-2 with respect to the line 57-2. In some embodiments, a slope of a medial line 66 that is computed between the medial position sensor 39-2 and the line 57-2 can be determined and can be used to determine the change in position of the medial position sensor 39-2. For example, as depicted in FIG. 4, if the apex 75 of the heart 10 moves such that the medial position sensor 39-2 moves towards the top side 47-2 or base side 48-2 of the top/base axis, or another axis, depending on the position of the heart 10, the slope of the medial line 66 can change, which can be used to determine a particular movement of the medial position sensor 39-2 in a direction of arrow 65 and heart 10.

In some embodiments, a medial position sensor positional change vector can be calculated based on the change in position of the medial position sensor 39-2 with respect to the line 57-2 between the proximal position sensor 40-2 and the distal position sensor 17-2. In an example, the medial position sensor positional change vector can be representative of the change in position of the medial position sensor 39-2 in the direction of arrow 65 and can be used to rotationally shift a cardiac model so it reflects movement of the heart 10, as discussed further in relation to FIG. 5.

Figure 5:
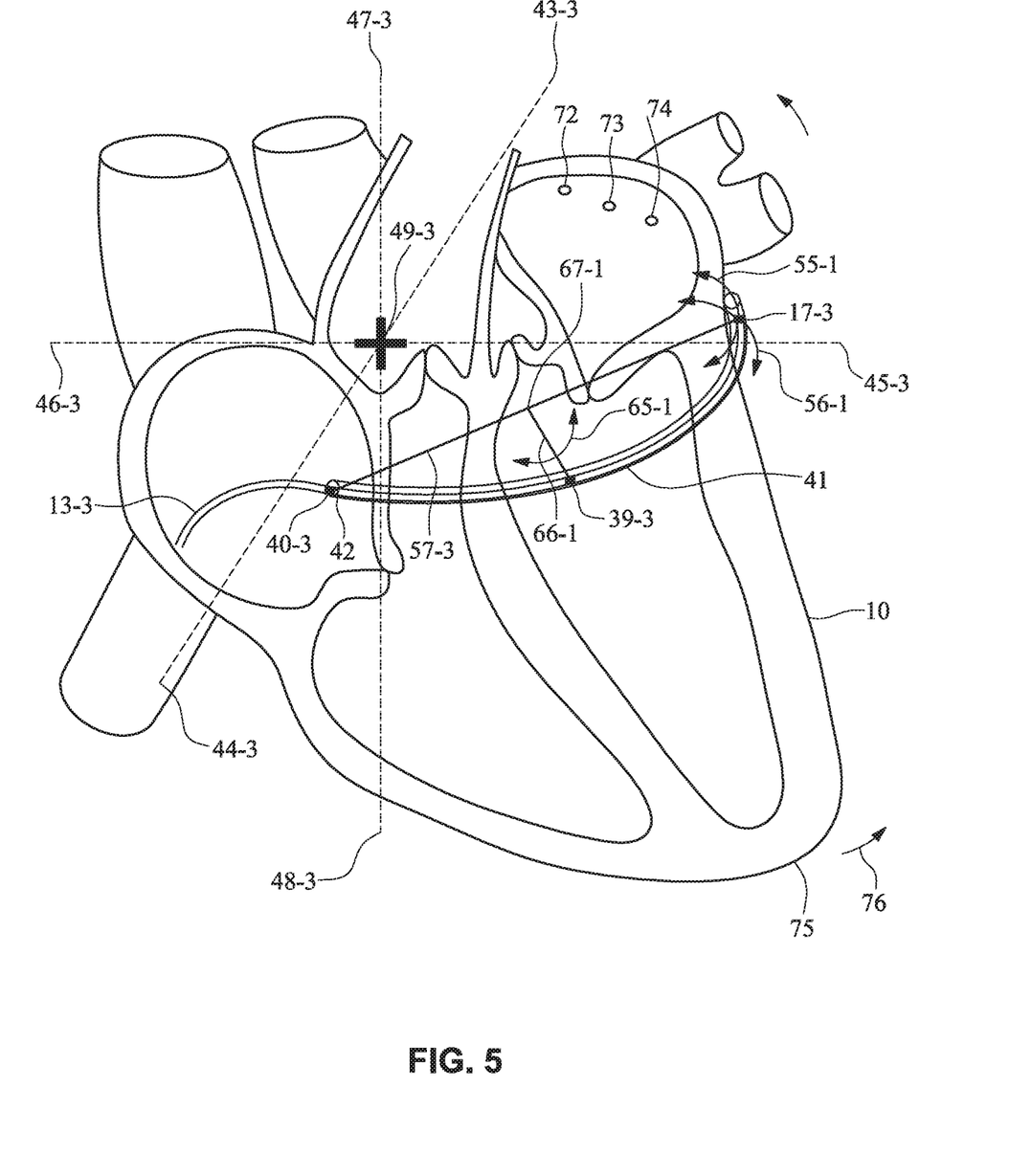
FIG. 5 depicts the heart in FIG. 2 with the catheter inserted in the coronary sinus of the heart and movement of the medial electrode and movement of the distal electrode, in accordance with embodiments of the present disclosure.

FIG. 5 depicts the heart in FIG. 2 with a catheter 13-3 inserted in the coronary sinus 41 of the heart and movement of a medial position sensor 39-3 with respect to a computed line 57-3 between the proximal position sensor 40-3 disposed on the distal end of the catheter 13-3 and the distal position sensor 17-3 disposed on the distal end of the catheter 13-3 and movement of the distal position sensor 17-3 with respect to the proximal position sensor 40-3, in accordance with embodiments of the present disclosure. As discussed herein, the change in coordinates of the proximal position sensor 40-3 can be used to linearly shift a cardiac model so it reflects movement of the heart 10. In addition, the distal position sensor positional change vector can be representative of the change in position of the distal position sensor 17-3 and can be used to shift the cardiac model so it reflects movement of the heart 10. Further, the medial position sensor positional change vector can be representative of the change in position of the medial position sensor 39-3 and can be used to shift the cardiac model so it reflects movement of the heart 10.

In some embodiments, one or more fiducial points can be located on the cardiac model (e.g., fiducial points 72, 73, 74). In some embodiments, a geometry of the cardiac model can be determined, which can reflect a surface of the cardiac model. A location (e.g., coordinates) of the fiducial points 72, 73, 74 and/or the geometry of the cardiac model can be referenced to a location of the proximal position sensor 40-3. As the proximal position sensor 40-3 moves, a change in position of the proximal position sensor can be determined based on the initial position signal and the subsequent position signal. The change in location of the proximal position sensor 40-3 can be translated to the geometry of the cardiac model and/or the location of the fiducial points 72, 73, 74 associated with the cardiac model and the geometry and/or the fiducial points 72, 73, 74 can be linearly shifted based on the change in location of the proximal position sensor 40-3. In an example, if the position of the proximal position sensor 40-3 changes by $x_1$, $y_1$, $z_1$, the geometry of the cardiac model and/or the location of the fiducial points 72, 73, 74 can be linearly shifted by $x_1$, $y_1$, $z_1$. For instance, if the heart 10 moves up toward the top side 47-3 of the top/base axis, the change in position of the proximal position sensor can be translated to the geometry of the cardiac model and/or the location of the fiducial points 72, 73, 74 to linearly shift the cardiac model of the heart 10 up toward the top side 47-3 of the top/base axis.

In some embodiments, the distal position sensor positional change vector can be representative of the change in position of the distal position sensor 17-3 and can be used to rotationally shift the cardiac model so it reflects movement of the heart 10. In an example, the distal position sensor positional change vector can represent a rotation of the heart around the proximal position sensor 40-3. For example, the distal position sensor positional change vector can be in a direction of arrows 55-1, 56-1 or a direction between the arrows 55-1, 56-1.

The distal position sensor positional change vector can be used to rotate the model of the heart 10 around the proximal position sensor 40-3. For instance, if the heart 10 moves up toward the top side 47-3 of the top/base axis, the change in position of the proximal position sensor 40-3 can be translated to the geometry of the cardiac model and/or the location of the fiducial points 72, 73, 74 to also linearly shift the cardiac model of the heart 10 up toward the top side 47-3 of the top/base axis. Additionally, if the apex 75 of the heart 10 rotates up in a direction of arrow 76, the movement of the heart 10 can be detected via the change in position of the distal position sensor 17-3 and can be accounted for via the distal position sensor positional change vector. In an example, the cardiac model can be rotationally shifted via the distal position sensor positional change vector. For instance, the distal position sensor 17-3 can provide a distal position sensor positional change vector that originates from a location of the distal position sensor 17-3 associated with the initial position signal.

As such, the geometry and/or the fiducial points 72, 73, 74 of the cardiac model can be linearly shifted based on the change in location of the proximal position sensor 40-3 and the cardiac model can be rotationally shifted by applying the distal position sensor positional change vector to the location of the cardiac model associated with the initial position signal of the distal position sensor 17-3. In some embodiments, the initial position signal of the distal position sensor 17-3 can be correlated with a location on the cardiac model. The correlated location of the distal position sensor 17-3 on the cardiac model can be rotationally shifted in a manner similar to the fiducial points 72, 73, 74. For example, the correlated location of the distal position sensor 17-3 on the cardiac model can be linearly shifted by $x_1$, $y_1$, $z_1$ based on the change in location of the proximal position sensor 40-3, as discussed herein. Upon shifting of the correlated location of the distal position sensor 17-3 on the cardiac model, the distal position sensor positional change vector can be applied to the shifted correlated location of the distal position sensor 17-3. Thus, the cardiac model can be rotated via the distal position sensor positional change vector about the proximal position sensor 40-3.

In some embodiments, the medial position sensor positional change vector can be representative of the change in position of the medial position sensor 39-3 and can be used to shift the cardiac model so it reflects movement of the heart 10. In an example, the medial position sensor positional change vector can represent a rotation of the heart 10 around the computed line 57-3 between the proximal position sensor 40-3 and the distal position sensor 17-3. For example, the medial position sensor positional change vector can be in a direction of arrow 65-1. The medial position sensor positional change vector can be used to rotate the model of the heart 10 around the computed line 57-3. For instance, if the heart 10 moves up toward the top side 47-3 of the top/base axis, the change in position of the proximal position sensor 40-3 can be translated to the geometry of the cardiac model and/or the location of the fiducial points 72, 73, 74 to also move the cardiac model of the heart 10 up toward the top side 47-3 of the top/base axis. Additionally, if the apex of the heart 75 rotates from a posterior side 43-3 to an anterior side 44-3 or the anterior side 44-3 to the posterior side 43-3, the movement of the heart 10 can be detected via the change in position of the medial position sensor 39-3 and can be accounted for via the medial position sensor positional change vector. In an example, the cardiac model can be rotated via the medial position sensor positional change vector. For instance, the medial position sensor 39-3 can provide a distal position sensor positional change vector that can originate from a location of the medial position sensor 39-3 associated with the initial position signal.

As such, the geometry and/or the fiducial points 72, 73, 74 of the cardiac model can be shifted based on the change in location of the proximal position sensor 40-3 and the cardiac model can be rotated by applying the medial position sensor positional change vector to the location of the cardiac model associated with the initial position signal of the medial position sensor 39-3. In some embodiments, the initial position signal of the medial position sensor 39-3 can be correlated with a location on the cardiac model. The correlated location of the medial position sensor 17-3 on the cardiac model can be shifted in a manner similar to the fiducial points 72, 73, 74, For example, the correlated location of the distal position sensor 17-3 on the cardiac model can be linearly shifted by $x_1$, $y_1$, $z_1$, as discussed herein. Upon linearly shifting the correlated location of the medial position sensor 39-3 on the cardiac model, the medial position sensor positional change vector can be applied to the shifted correlated location of the medial position sensor 39-3. As such, the cardiac model can be rotationally shifted via the medial position sensor positional change vector around the computed line between the proximal position sensor 40-3 and the distal position sensor 17-3.

Accordingly, the cardiac model (e.g., fiducial points 72, 73, 74 and/or a geometry of the cardiac model) can be shifted. In some embodiments, the cardiac model can be linearly shifted and/or rotationally shifted. For example, the cardiac model can be linearly shifted based on the change in position of the proximal position sensor 40-3. The change in position of the proximal position sensor 40-3 can be defined by a linear change in coordinates. For example, the proximal position sensor 40-3 can be moved along the top/base axis in a direction of the top side 47-3 or base side 48-3; along the anterior/posterior axis in a direction of the posterior side 43-3 or anterior side 44-3; and/or along the left/right axis in a direction of the left side 45-3 or right side 46-3.

The cardiac model can be rotationally shifted based on the change in position of the distal position sensor 17-3 and/or the medial position sensor 39-3. For example, as discussed herein, the distal position sensor positional change vector can be applied to the correlated and linearly shifted location of the distal position sensor 17-3 and the cardiac model can be rotationally shifted via the distal position sensor positional change vector about the proximal position sensor 40-3. For instance, the cardiac model can be rotationally shifted in a direction of one of arrows 55-1, 56-1. In addition, the medial position sensor positional change vector can be applied to the correlated and linearly shifted location of the medial position sensor 39-3 and the cardiac model can be rotationally shifted via the medial position sensor positional change vector about the computed line 57-3 between the proximal position sensor 40-3 and the distal position sensor 17-3 in a direction of arrow 65-1.

Figure 6:
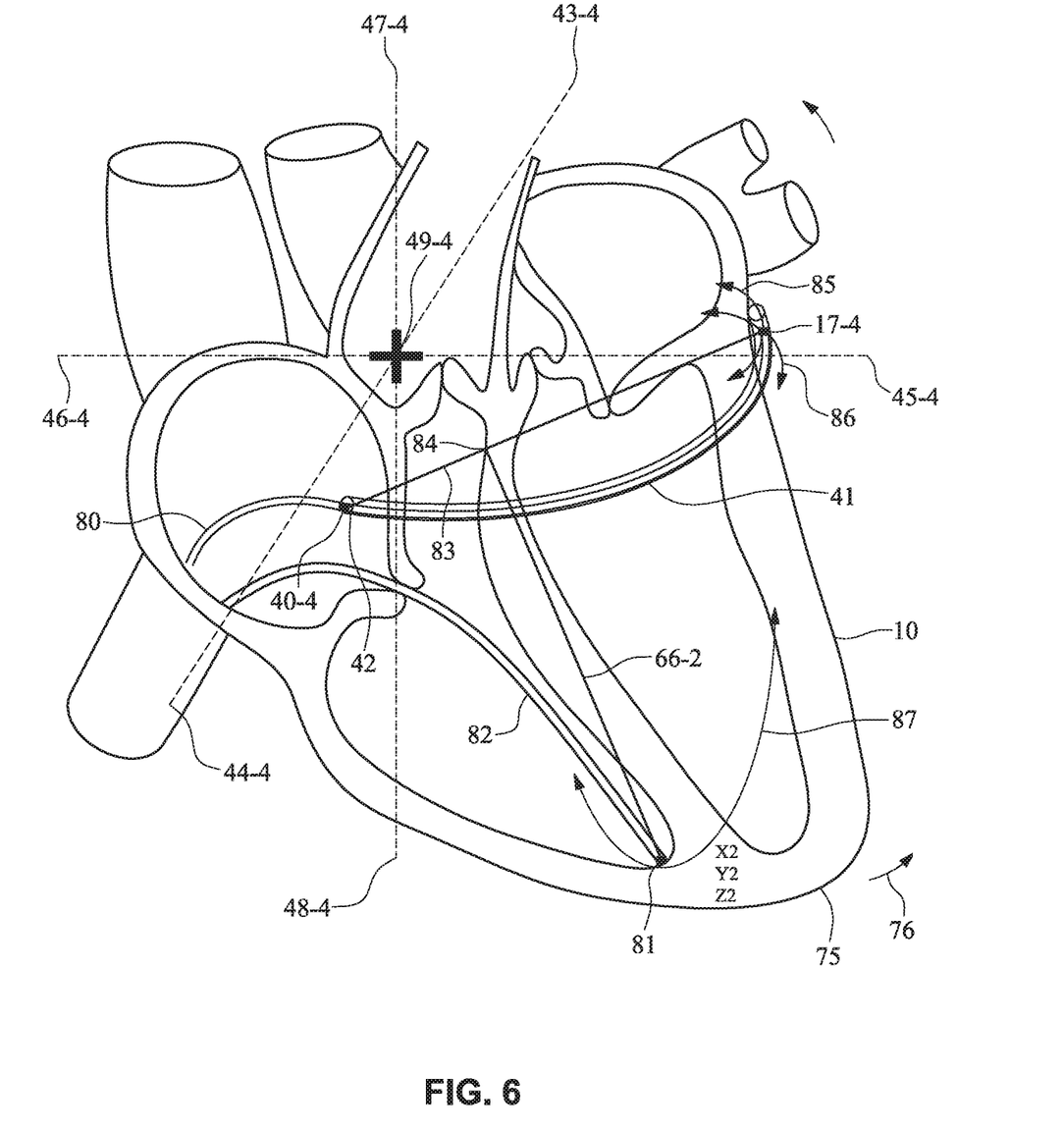
FIG. 6 depicts the heart in FIG. 2 with a catheter inserted in the coronary sinus of the heart and movement of a distal electrode disposed on the distal end of the catheter and movement of a medial electrode disposed on a distal end of a right ventricle apex catheter, in accordance with embodiments of the present disclosure.

FIG. 6 depicts the heart 10 in FIG. 2 with a catheter 80 inserted in the coronary sinus 41 of the heart 10 and movement of a distal position sensor 17-4 disposed on the distal end of the catheter 80 with respect to a proximal position sensor 40-4 disposed on the distal end of the catheter 80 and movement of a medial position sensor 81 disposed on a distal end of a right ventricle apex catheter 82 with respect to a computed line 83 between the proximal position sensor 40-4 and the distal position sensor 17-4, in accordance with embodiments of the present disclosure. As discussed in relation to FIGS. 2 to 5, the medial position sensor 81 can be disposed on the distal end of the coronary sinus catheter. In some embodiments, the medial position sensor 81 can be located on the distal. end of the right ventricle apex catheter 82.

In some embodiments, the medial position sensor 81 can be placed on a different catheter (e.g., right ventricle apex catheter 82). The medial position sensor 81 disposed on the right ventricle apex catheter 82 can offer an additional advantage in accuracy in shifting a point of interest associated with a cardiac model. For example, the medial position sensor 81 disposed on the distal end of the right ventricle apex catheter 82 can be located a further distance from the computed line 83 and the proximal position sensor 40-4 and the distal position sensor 17-4. As such, errors associated with a position of the medial position sensor 81 can be lessened over the greater distance from the computed line 83 and the proximal position sensor 40-3 and the distal position sensor 17-4.

In some embodiments, a medial locating signal can be received from the proximal position sensor 40-4 and the distal position sensor 17-4 before the initial position signal is received from the proximal position sensor 40-4, the distal position sensor 17-4, and the medial position sensor 81. The medial locating signal can include a position signal received from. the proximal position sensor 40-4 and the distal position sensor 17-4. Based on the position signal received from the proximal position sensor 40-4 and the distal position sensor 17-4, the medial position sensor 81 can be selected. For example, a line between the proximal position sensor 40-4 and the distal position sensor 17-4 can be determined.

A midpoint 84 of the line 83 between the proximal position sensor 40-4 and the distal position sensor 17-4 can be determined and the medial position sensor 81 can be placed in the right ventricle apex selected based off of the midpoint of the line 83. In some embodiments, the midpoint 84 of the line 83 can be defined as a point between the proximal position sensor 40-4 and the distal position sensor 17-4. In some embodiments, the midpoint 84 of the line 83 can be a point that is located approximately in the middle of the proximal position sensor 40-4 and the distal position sensor 17-4; nearer to the proximal position sensor 40-4; or nearer to the distal position sensor 17-4. In some embodiments, the right ventricle apex catheter 82 can include a plurality of position sensors disposed along a distal end of the right ventricle apex catheter 82 and one of the plurality of position sensors can be selected based off of the midpoint 84 of the line 83. In an example, a position of the proximal position sensor 40-4 (e.g., $x_p$, $y_p$, $z_p$) and a position of the distal position sensor 17-4 (e.g., (e.g., $x_d$, $y_d$, $z_d$) can be determined and the midpoint 84 can be calculated. Based on the midpoint 84, the medial position sensor 81 can be selected from a plurality of position sensors disposed on the right ventricle apex catheter 82. For example, the medial position sensor 81 that is selected can be orthogonal to the midpoint 84 or close to orthogonal to the midpoint 84 with respect to the line 83.

As discussed herein and in relation to FIG. 5, the change in coordinates of the proximal position sensor 40-4 can be used to shift a cardiac model so it reflects movement of the heart 10. In addition, the distal position sensor positional change vector can be representative of the change in position of the distal position sensor 17-4 and can be used to shift the cardiac model so it reflects movement of the heart. 10. The distal position sensor positional change vector can be in a direction of arrows 85, 86 or a direction between arrows 85, 86. In some embodiments, the medial position sensor positional change vector can be representative of the change in position of the medial position sensor 81 and can be used to shift the cardiac model so it reflects movement of the heart 10. In an example, the medial position sensor positional change vector can represent a rotation of the heart 10 around the computed line 83 between the proximal position sensor 40-4 and the distal position sensor 17-4. For example, the medial position sensor positional change vector can be in a direction of arrow 87.

Figure 7:
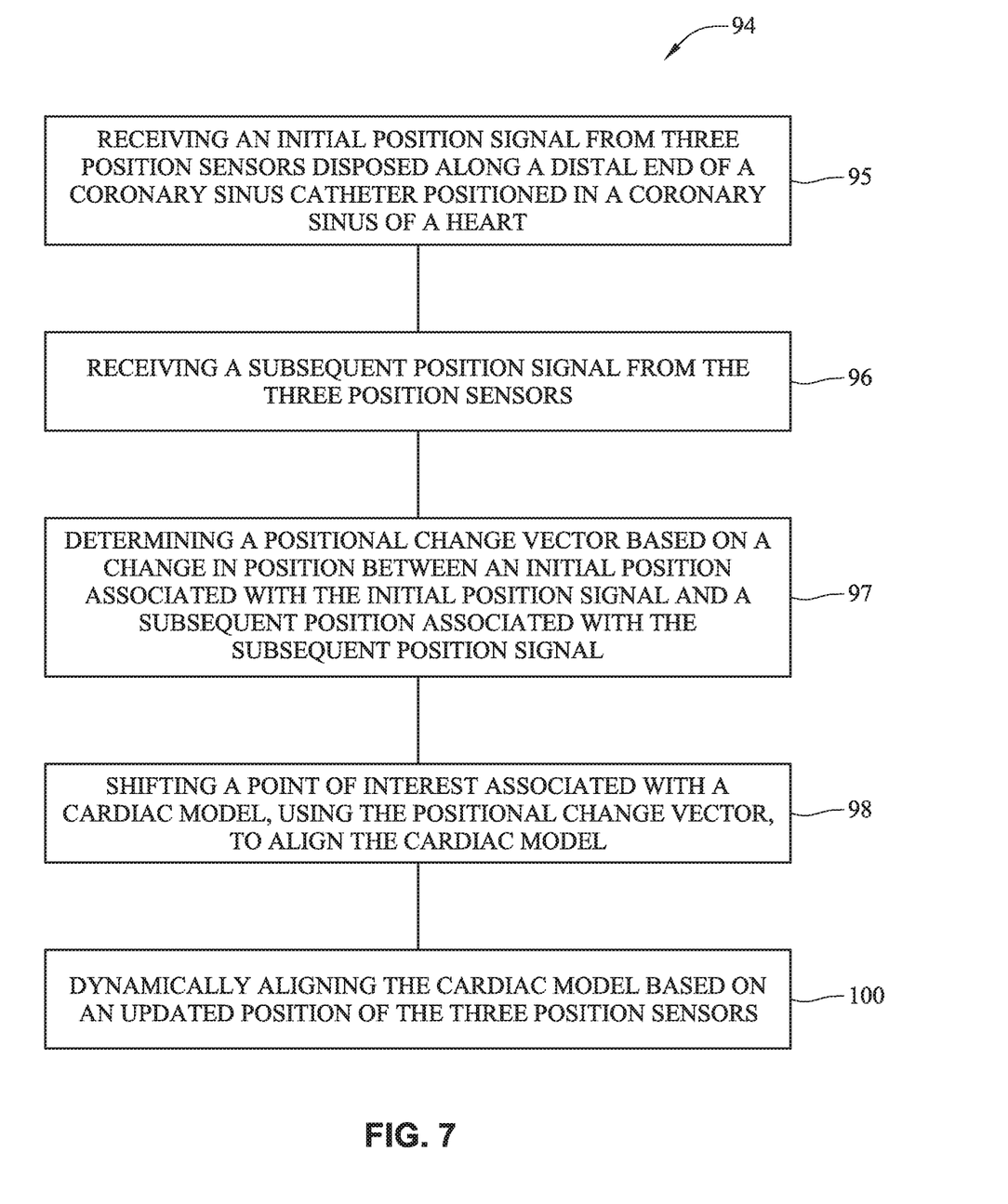
FIG. 7 depicts a block diagram of an example of a method for aligning a cardiac model, in accordance with embodiments of the present disclosure.

FIG. 7 depicts a block diagram of an example of a method 94 for aligning a cardiac model, in accordance with embodiments of the present disclosure. In some embodiments, at block 95, the method 94 can include receiving an initial position signal from three position sensors disposed along a distal end of a coronary sinus catheter positioned in a coronary sinus of a heart. The position sensors can be magnetic based (e.g., a coil) and/or impedance based (e.g., an electrode). In an example, the initial position signal can be received from a proximal position sensor, a distal position sensor, and a medial position sensor. The medial position sensor can be disposed between the proximal position sensor and the distal position sensor. The proximal position sensor, the distal position sensor, and the medial position sensor can be longitudinally spaced along the coronary sinus catheter.

In some embodiments, a medial locating signal can be received from the proximal position sensor and the distal position sensor, as discussed in relation to FIG. 2. The medial locating signal can include a position signal received from the proximal position sensor and the distal position sensor. The medial locating signal can be used to determine a line between the proximal position sensor and the distal position sensor and a midpoint of the line between the proximal position sensor and the distal position sensor. In some embodiments, the method 94 can include selecting the medial position sensor based on the midpoint of the line between the proximal position sensor and the distal position sensor. In an example, the coronary sinus catheter can include a plurality of position sensors. For instance, the coronary sinus catheter can include 8 to 10 position sensors that are disposed on the coronary sinus catheter and are located within the coronary sinus. In some embodiments, one of the plurality of position sensors can be selected as the medial position sensor, based on the midpoint of the line between the proximal position sensor and the distal position sensor. In some embodiments, the midpoint of the line between the proximal position sensor and the distal position sensor may be in a center between the proximal position sensor and the distal position sensor or may be disposed closer to the proximal position sensor or the distal position sensor from the center of the line between the proximal position sensor and the distal position sensor.

In some embodiments, the method 94 can include receiving a subsequent position signal from the three position sensors, at block 96. The position of the heart can change between the initial position signal and the subsequent position signal in some embodiments. In some embodiments, as discussed herein, the heart can be fixed at a top of the heart via various vessels, which can cause the heart to rotate around a position generally located in the pulmonary artery to the right of the pulmonic valve, as further shown in FIG. 2. In some embodiments, the initial position signal and the subsequent position signal can be received from the proximal position sensor placed in a coronary sinus ostium of the heart. In an example, the coronary sinus ostium can include features that are recognizable by a physician, which can allow the physician to place the proximal position sensor in proximity to the coronary sinus ostium and keep the proximal position sensor in that position to provide a reference point with respect to the distal position sensor and the medial position sensor.

In some embodiments, the method 94 can include determining a positional change vector based on a change in position between an initial position associated with the initial position signal and a subsequent position associated with the subsequent position signal, at block 97. In some embodiments, the cardiac model can be linearly shifted and/or rotationally shifted via the determined positional change vectors. For example, the cardiac model can be linearly shifted based on the change in position of the proximal position sensor. The change in position of the proximal position sensor can be defined by a linear change in coordinates, which can be used to determine a linear positional change vector. For example, as discussed herein, with reference to the axes in FIGS. 2 to 6, the proximal position sensor can be moved along the top/base axis in a direction of the top side or base side; along the anterior/posterior axis in a direction of the posterior side or anterior side; and/or along the left/right axis in a direction of the left side or right side. The method 94 can include shifting a point of interest associated with the cardiac model, using the positional change vector, at block 98. For example, a point on the cardiac model corresponding to the position of the proximal position sensor can be shifted based on the change in position of the proximal position sensor.

In some embodiments of the present disclosure, the method 94 can include dynamically aligning the cardiac model based on an updated position of the three position sensors, at block 100. For example, embodiments of the present disclosure can dynamically shift the point of interest associated with the cardiac model to ensure that a position associated with the point of interest remains consistent with an actual position of the heart 10. Embodiments of the present disclosure can check for updates regarding a change in position of the position sensors at defined intervals. In some embodiments, the check for updates can be performed continuously, while in some embodiments the check for updates can be performed intermittently at defined time intervals. Thus, embodiments of the present disclosure can check for updates in the position of the position sensors and can update the position of the cardiac model in accordance with the updated position of the position sensors. For example, as the heart changes position within the chest of the patient, the position of the position sensors can change from the initial position, to the subsequent position, to another position (e.g., an updated position). Accordingly, the cardiac model can be dynamically aligned such that it reflects the actual position of the heart 10.

The cardiac model can be rotationally shifted based on the change in position of the distal position sensor and/or the medial position sensor. In some embodiments, a change in position of the distal position sensor can be determined with respect to the proximal position sensor and can be used to determine a rotational positional change vector. In some embodiments, a slope of a line extending between the proximal position sensor and the distal position sensor can be determined, which can be used to determine a change in position of the distal position sensor with respect to the proximal position sensor. A distal position sensor positional change vector can be calculated based on the change in position of the distal position sensor with respect to the proximal position sensor. The distal position sensor positional change vector can be used to shift a point of interest associated with the cardiac model, using the positional change vector. For example, as discussed herein, the distal position sensor positional change vector can be applied to the correlated and shifted location of the distal position sensor and the cardiac model can be rotationally shifted via the distal position sensor positional change vector about the proximal position sensor, as discussed in relation to FIG. 5.

Some embodiments include calculating a medial position sensor positional change vector, based on the change in position of the medial position sensor with respect to the line between the proximal position sensor and the distal position sensor. The medial positional change vector can be a rotational positional change vector in some embodiments. The medial position sensor positional change vector can be used to shift a point of interest associated with the cardiac model, using the positional change vector. In an example, the medial position sensor positional change vector can be applied to the shifted correlated location of the medial position sensor and the cardiac model can be rotationally shifted via the medial position sensor positional change vector about the computed line between the proximal position sensor and the distal position sensor using the medial position sensor positional change vector.

Figure 8:
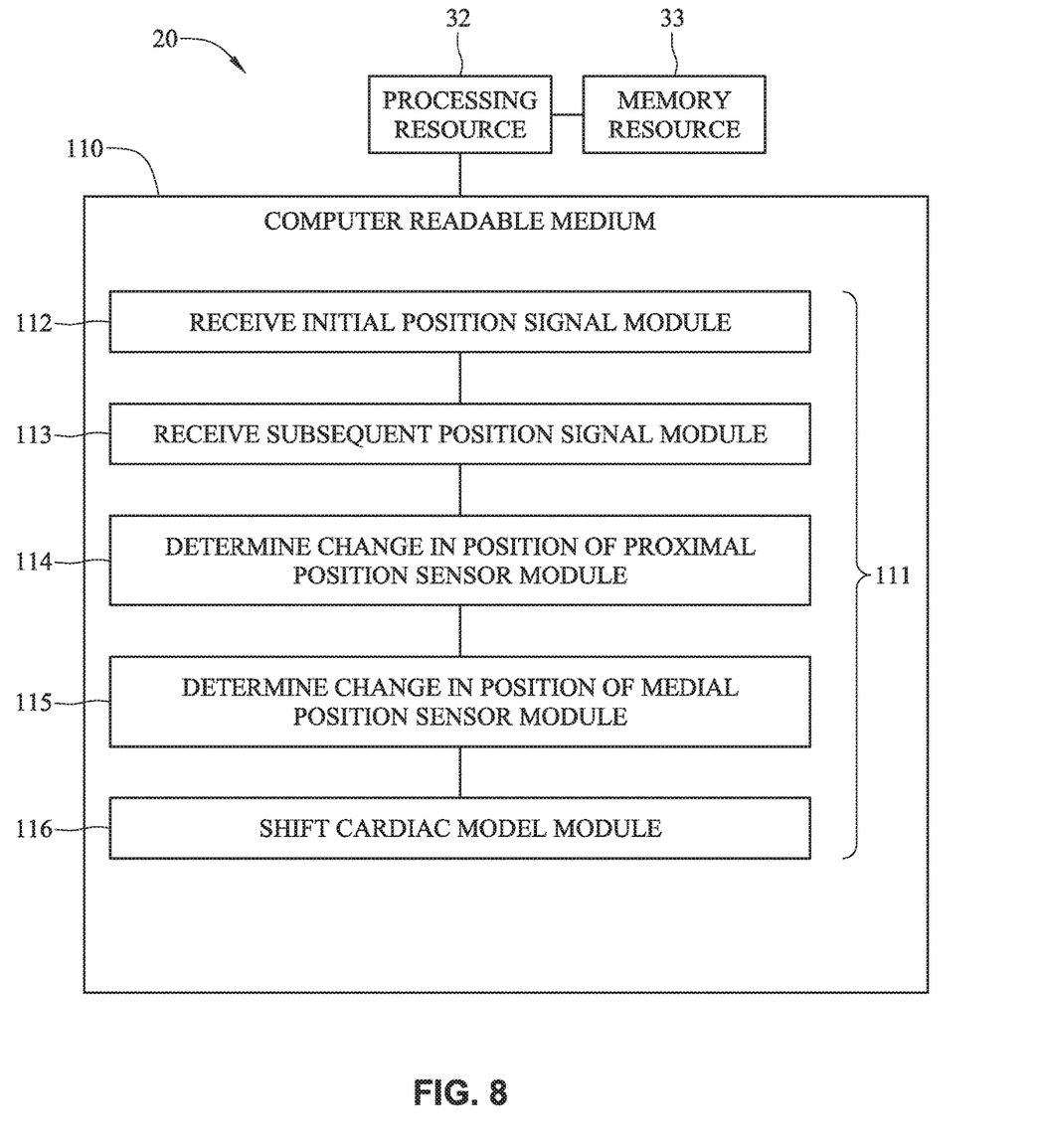
FIG. 8 illustrates a block diagram of an example of a computer-readable medium in communication with process-

FIG. 8 illustrates a block diagram of an example of a computer-readable medium in communication with processing resources of a computing device, in accordance with embodiments of the present disclosure. The computer system 20, as discussed in relation to FIG. 1, can utilize software, hardware, firmware, and/or logic to perform a number of functions. The computer system 20 can include a number of remote computing devices.

The computer system 20 can be a combination of hardware and program instructions configured to perform a number of functions. The hardware, for example, can include one or more processing resources 32, computer readable medium (CRM) 110, etc. The program instructions (e.g., computer-readable instructions (CRI) 111) can include instructions stored on CRM 110 and executable by the processing resource 32 to implement a desired function (e.g., determine a change in position of the proximal position sensor based on the initial position signal and the subsequent position signal, etc.). The CRI 110 can also be stored in remote memory managed by a server and can represent an installation package that can be downloaded, installed, and executed. The computer system 20 can include memory resources 33, and the processing resources 32 can be coupled to the memory resources 33.

Processing resources 32 can execute CRI 111 that can be stored on an internal or external non-transitory CRM 110. The processing resources 32 can execute CRI 111 to perform various functions, including the functions described with respect to 1 to FIG. 7.

A number of modules 112, 113, 114, 115, 116 can be sub-modules or other modules. For example, the receive initial position signal module 112 and the receive subsequent position signal module 113 can be sub-modules and/or contained within a single module. Furthermore, the number of modules 112, 113, 114, 115, 116 can comprise individual modules separate and distinct from one another.

A receive initial position signal module 112 can comprise CRI 111 and can be executed by the processing resource 32 to receive an initial position signal from a proximal position sensor, a distal position sensor, and a medial position sensor. The proximal position sensor can be disposed in a coronary sinus of a heart in some embodiments. The proximal position sensor can serve as a reference point to the distal position sensor and the medial position sensor, as discussed herein. In some embodiments, the medial position sensor can be disposed orthogonally to a computed line extending between the proximal position sensor and the distal position sensor.

In some embodiments, the medial position sensor can be disposed on a distal end of a coronary sinus catheter between the proximal position sensor and the distal position sensor. In some embodiments, the proximal position sensor and the distal position sensor are disposed on a distal end of a coronary sinus catheter. In some embodiments, the medial position sensor can be disposed on a distal end of a right ventricle apex catheter. The medial position sensor can be positioned orthogonally from a midpoint of the computed line between the proximal position sensor and the distal position sensor.

A receive subsequent position signal module 113 can comprise CRI 111 and can be executed by the processing resource 32 to receive a subsequent position signal from the proximal position sensor, the distal position sensor, and the medial position sensor. In some embodiments, the proximal position sensor, the distal position sensor, and the medial position sensor can be moved between receipt of the initial position signal and receipt of the subsequent position signal. As such, the change in position between the receipt of the initial position signal and receipt of the subsequent position signal can be captured.

A determine change in position module of proximal position sensor module 114 can comprise CRI 111 and can be executed by the processing resource 32 to determine a change in position of the proximal position sensor based on the initial position signal and the subsequent position signal. In some embodiments, a change in a position of the distal position sensor can be determined with respect to the proximal position sensor based on the initial position signal and the subsequent position signal. In some embodiments, the change in the position of the distal position sensor with respect to the proximal position sensor can include a determination of a change in slope between the proximal position sensor and the distal position sensor.

A determine change in position of medial position sensor module 115 can comprise CRI 111 and can be executed by the processing resource 32 to determine a change in position of the medial position sensor with respect to the line extending between the proximal position sensor and the distal position sensor. In some embodiments, as discussed herein, a medial position sensor positional change vector can be determined based on the change in position of the medial position sensor. The medial positional change vector can be a rotational positional change vector in some embodiments.

A shift cardiac model module 116 can comprise CRI 111 and can be executed by the processing resource 32 to shift a cardiac model based on the change in position of the proximal position sensor and the change in the position of the medial position sensor with respect to the line extending between the proximal position sensor and the distal position sensor. In some embodiments, the cardiac model can be shifted to reflect an actual position and/or orientation of the heart. In some embodiments, the cardiac model can be continually updated to reflect changes in the position and/or orientation of the heart.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated. embodiments. However, surgical instruments may be used in many orientations and positions, and these terms are not intended to be limiting and absolute.

Although at least one embodiment of aligning a cardiac model has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for aligning a cardiac model, comprising:
receiving an initial position signal from three position sensors disposed along a distal end of a coronary sinus catheter positioned in a coronary sinus of a heart;
receiving a subsequent position signal from the three position sensors disposed along the distal end of the coronary sinus catheter positioned in the coronary sinus of the heart;
determining a positional change vector based on a change in position between an initial position associated with the initial position signal and a subsequent position associated with the subsequent position signal; and
shifting a point of interest associated with the cardiac model, using the positional change vector, to align the cardiac model with a position and orientation of the heart associated with the subsequent position signal.

2. The method of claim 1, wherein the three position sensors include a proximal electrode, a distal electrode, and a medial electrode longitudinally spaced along the coronary sinus catheter, the proximal electrode being proximal to the distal electrode and the medial electrode, and the medial electrode being proximal to the distal electrode and distal to the proximal electrode.

3. The method of claim 2, wherein the method includes receiving the initial position signal and the subsequent position signal from the proximal electrode, the distal electrode, and the medial electrode.

4. The method of claim 2, wherein receiving the initial position signal and the subsequent position signal includes receiving the signals from the proximal electrode disposed in a coronary sinus ostium of the heart.

5. The method of claim 4, further comprising:
determining a change in position of the proximal electrode; and
shifting a point on the cardiac model corresponding to the position of the proximal electrode, based on the change in position of the proximal electrode.

6. The method of claim 2, further comprising:
determining a change in position of the distal electrode with respect to the proximal electrode; and
calculating a distal electrode positional change vector, based on the change in position of the distal electrode with respect to the proximal electrode.

7. The method of claim 6, further comprising shifting the cardiac model using the distal electrode positional change vector.

8. The method of claim 2, further comprising:
determining a line between the proximal electrode and the distal electrode; and
determining a midpoint of the line between the proximal electrode and the distal electrode.

9. The method of claim 8, further comprising selecting the medial electrode based on the midpoint of the line between the proximal electrode and the distal electrode, such that a location signal can be received from the medial electrode.

10. The method of claim 9, further comprising calculating a medial electrode positional change vector, based on the change in position of the medial electrode with respect to the line between the proximal electrode and the distal electrode.

11. The method of claim 10, further comprising shifting the cardiac model using the medial electrode positional change vector.

* * * * *